(12) United States Patent
McGillicuddy (10) Patent No.: US 11,759,214 B2
(45) Date of Patent: Sep. 19, 2023

(54) FLEXIBLE CANNULA WITH DOUBLE HELIX SPRING COIL

(71) Applicant: Cervos Medical LLC, Marshfield, MA (US)

(72) Inventor: Andrew McGillicuddy, Humarock, MA (US)

(73) Assignee: CERVOS MEDICAL LLC, Marshfield, MA (US)

( * ) Notice: Subject to any disclaimer, the term of this patent is extended or adjusted under 35 U.S.C. 154(b) by 0 days.

(21) Appl. No.: 16/881,865

(22) Filed: May 22, 2020

(65) Prior Publication Data

US 2020/0367914 A1 Nov. 26, 2020

Related U.S. Application Data

(60) Provisional application No. 62/851,787, filed on May 23, 2019.

(51) Int. Cl.
*A61B 17/16* (2006.01)
*A61B 17/34* (2006.01)
(Continued)

(52) U.S. Cl.
CPC ...... *A61B 17/1631* (2013.01); *A61B 17/1637* (2013.01); *A61B 2017/00424* (2013.01); *A61B 2017/3454* (2013.01); *A61B 2217/005* (2013.01); *A61M 25/0102* (2013.01); *A61M 2202/10* (2013.01)

(58) Field of Classification Search
CPC ............ A61B 17/1631; A61B 17/1633; A61B 17/1637; A61B 2017/00424; A61B 2017/3454; A61B 2217/005
See application file for complete search history.

(56) References Cited

U.S. PATENT DOCUMENTS

| 10,231,716 B2 | 3/2019 | McGillicuddy et al. |
| 10,556,046 B2 | 2/2020 | McGillicuddy et al. |

(Continued)

FOREIGN PATENT DOCUMENTS

| WO | 2010138895 A2 | 12/2010 |
| WO | 2014070804 A1 | 5/2014 |

(Continued)

*Primary Examiner* — Kevin T Truong
*Assistant Examiner* — Diana Jones
(74) *Attorney, Agent, or Firm* — Hamilton, Brook, Smith & Reynolds, P.C.

(57) ABSTRACT

A flexible cannula device includes a solid cannula shaft, a solid cannula tip including an opening, and a coil positioned between and welded to the cannula shaft and cannula tip, the cannula shaft, coil, and cannula tip forming a lumen in fluid communication with the opening. A flexible cannulated drill includes a solid cannula shaft, a solid cannula tip shaped to drill through tissue, a coil positioned between and welded to the cannula shaft and cannula tip, and a handle connected to the cannula shaft. The coil can be a double helix coil comprising an inner coil within an outer coil. A tube inside the coil prevents fluid from leaking between rings of the coil. A cannula system includes an introducer needle and the flexible cannula device. A screw mechanism can adjust a length that the flexible cannula device extends beyond a distal end of the introducer needle.

25 Claims, 12 Drawing Sheets

(51) Int. Cl.
*A61M 25/01* (2006.01)
*A61B 17/00* (2006.01)

(56) References Cited

U.S. PATENT DOCUMENTS

| | | | |
|---|---|---|---|
| 2003/0191487 A1* | 10/2003 | Robison | A61B 17/32002 606/170 |
| 2010/0100098 A1* | 4/2010 | Norton | A61B 17/32002 606/86 R |
| 2011/0022026 A1* | 1/2011 | Sorensen | A61L 31/18 604/528 |
| 2012/0116247 A1* | 5/2012 | Wawrzyniak | A61B 10/025 600/567 |
| 2015/0289858 A1* | 10/2015 | McGillicuddy | A61B 10/025 600/566 |
| 2016/0106462 A1 | 4/2016 | McGillicuddy | |
| 2016/0361069 A1* | 12/2016 | Ardel | A61B 17/1617 |
| 2019/0314004 A1 | 10/2019 | McGillicuddy et al. | |
| 2020/0129680 A1 | 4/2020 | McGillicuddy et al. | |

FOREIGN PATENT DOCUMENTS

| | | | | |
|---|---|---|---|---|
| WO | 2015109100 A1 | 7/2015 | | |
| WO | WO-2015109100 A1 * | 7/2015 | | A61B 10/025 |

* cited by examiner

FLEXIBLE CANNULA WITH DOUBLE HELIX SPRING COIL

RELATED APPLICATIONS

This application claims the benefit of U.S. Provisional Application No. 62/851,787, filed on May 23, 2019. The entire teachings of the above application are incorporated herein by reference.

BACKGROUND

Bone is a hard material. It comprises a hard, outer layer called cortical bone and an inner, honeycomb structure called trabecular bone. Within the honeycomb structure is soft, spongy marrow, which is rich in stem cells. The different bones in the body of a person are varied in shape. Some bones, referred to as long bones, are barbell shaped, having an elongated shaft with either distal end being larger than the shaft. An example of a long bone is a femur. Some bones are flat, such as a hip bone or a shoulder blade. Some bones are disc shaped, such as bones found in the spine. The bones in the body are often connected by joints through such shapes as a ball and socket, as for example the hip and shoulder joints. Other joints have a different configuration and rely on tendons and ligaments to hold the bones together through the joint, for example, a knee joint. Orthopedic surgeons often need to access the bones and joints in the body to facilitate repair of the bone, joint tissue such as cartilage, ligaments and tendons. In addition, surgeons often wish to aspirate bone marrow from between the honeycomb trabecular bone to obtain a sample of stem cells often referred to as bone marrow aspirate.

SUMMARY

What is disclosed is a flexible cannula device. The flexible cannula can be made, on its distal and proximal ends, from a solid steel tube that defines a lumen. The flexible cannula can be made entirely from a wire coil. In one embodiment, a portion welded between the two ends of the cannula has a flexible section made from a wire coil. Preferably, the configuration is a coil within a coil or a double helix (double coil) configuration. The outer section of the double coil can have a winding in a certain orientation, for example clockwise. The inner section of the double coil can have a winding in the opposite orientation, for example counter clockwise. Rotational twisting forces on the double coil, whether clockwise or counterclockwise, will result in the two coils reacting to the forces in an opposing fashion. One direction of rotation may create forces that are directionally aligned to tighten the inner coil while at the same time loosening the outer coil. The fact that the two coils "fight against each other" in this manner helps keep the combined coil from distorting under rotational forces regardless of the direction of the forces. The thickness of the two wires to make the coils can be the same or different. Varying the thickness of the wires will provide more integrity to the coil in one directional force rotation than the opposite rotation. Generally, a thinner wire will provide more flexibility and a thicker wire more stiffness. Various lengths of coil are contemplated. A shorter section of coil will be stiffer and a longer section will be more flexible. For example, the entire cannula can be made of a coil or the coil can be welded between two solid ends and be relatively short in relation to the overall length of the assembled cannula. In addition, both inner and outer coils can be wound in the same orientation.

It is recognized that fluid (air or liquid) can pass through the space between the coils, e.g., the space between rings of each coil. In certain applications, for example, when aspirating tissue, this leaking of fluid between the coils is not desirable. In other applications, such as drilling, leaking of fluid between the coils is not an issue. To address the potential problem of air leaking when using an embodiment of the invention for aspiration, a thin-walled, flexible solid inner tube can run through the portion of the cannula that is made from the coil. This inner tube can run at least substantially the length of the cannula that is made of a coil. The tube provides a lumen for aspiration. For example, the thin-walled, solid tube can be made of a suitable polymer material, such as polyether ether ketone (PEEK), or more preferably, can be a thin-walled metal tube.

For example, in assembling the device, a first operation can include inserting a thin walled metal tube through the flexible coil and laser welding the tube to the flexible coil (steel-to-steel welding) on either end to secure the tube inside the flexible coil. The welds form an air tight seal on either end. Thus, the welds in this embodiment are on both ends of the coil to attach the inner, solid tube to the outer, wire wound tube on each end. The flexible coil can be a double coil as described herein. As a second operation, the flexible coil with the inner tube welded in place on either end of the coil can then be secured (e.g., welded) onto two other tubes on either end of the flexible coil, with the thin-walled solid tube running through the center of the coil, thus forming an aspiration cannula with a middle section that has a flexible coil, with a solid inner tube. In another embodiment, the inner, thin-walled tube can be longer than the coil, with one end molded into the handle of the device and the other end welded to the distal end of the coil. A cap can be welded onto the tip of the cannula. This cap also forms an air tight seal when one end of the solid, inner tube, proximal to the handle, is molded into the handle and the other end of the solid, inner tube, is welded to the coil on the distal end of the coil, the end of the coil farthest from the handle, i.e. the end of the coil closest to the tip of the cannula. Alternatively, the solid, inner tube opposite to the end molded into the handle can just dead-end inside the end of the coil very close to the end of the coil farthest from the handle. In an embodiment where a cap is welded onto the distal end of the coil, the solid, inner tube can dead-end just past the end of the coil and partially into the welded cap.

Figure 1A:
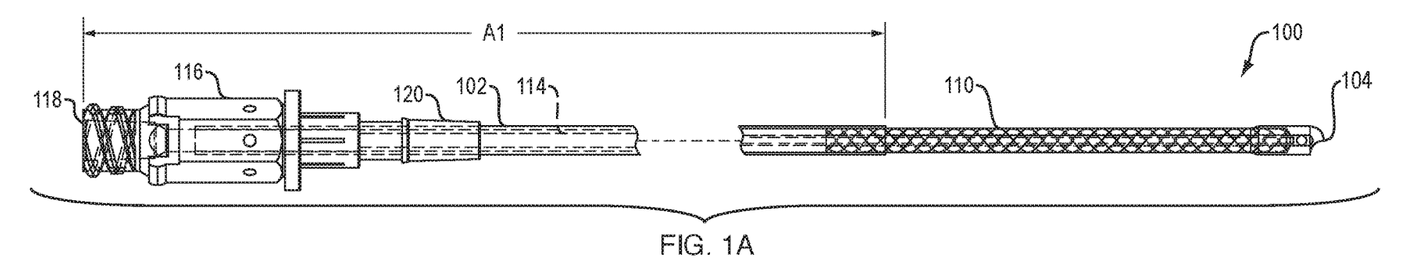
FIGS. 1A-1D illustrate several views of a flexible cannula device including an outer metal cannula, coil tubing, a cap, and an inner tube according to an example embodiment. The cap includes a closed end metal tip attached to the coil on the end of the coil, distal to the needle hub. The cap includes a cutting surface neat the tip and at least one side hole. The device includes a needle hub that can serve as a handle or support attachment of a larger, winged handle. A female luer connection is provided on the upper half of the needle hub and a male luer connection on the lower half of the needle hub opposite to the female luer connection, the male luer connection being closest to the coil and the female luer being furthest from the coil. The inner tube is molded into the needle hub handle on one end, runs substantially the length of the cannula and the coil, and dead ends inside the cap on the other end. The outer metal cannula is also molded into the needle hub and is attached (e.g., welded) to the coil on the other end.
Figure 1B:
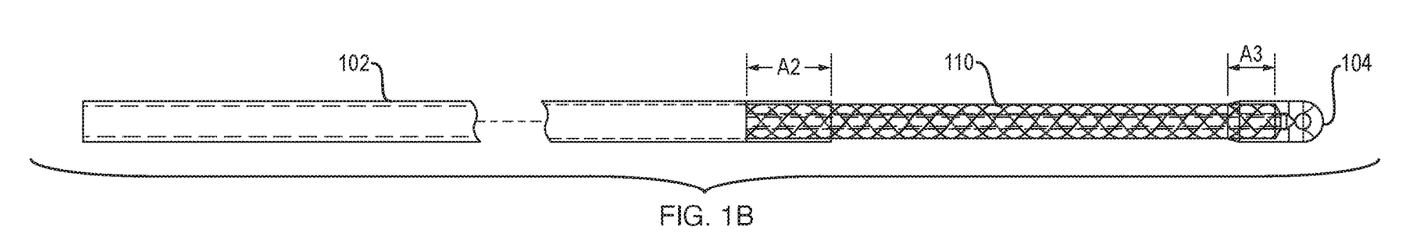
Figure 1C:
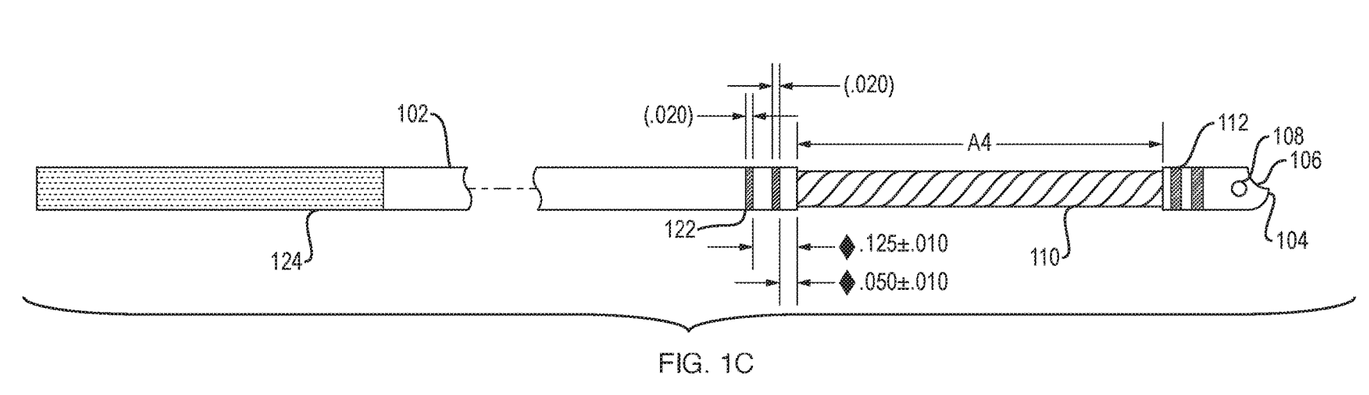
Figure 1D:
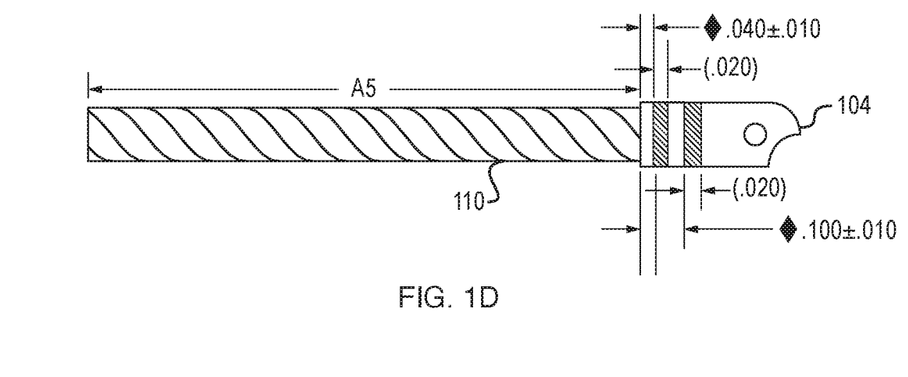
Figure 2A:
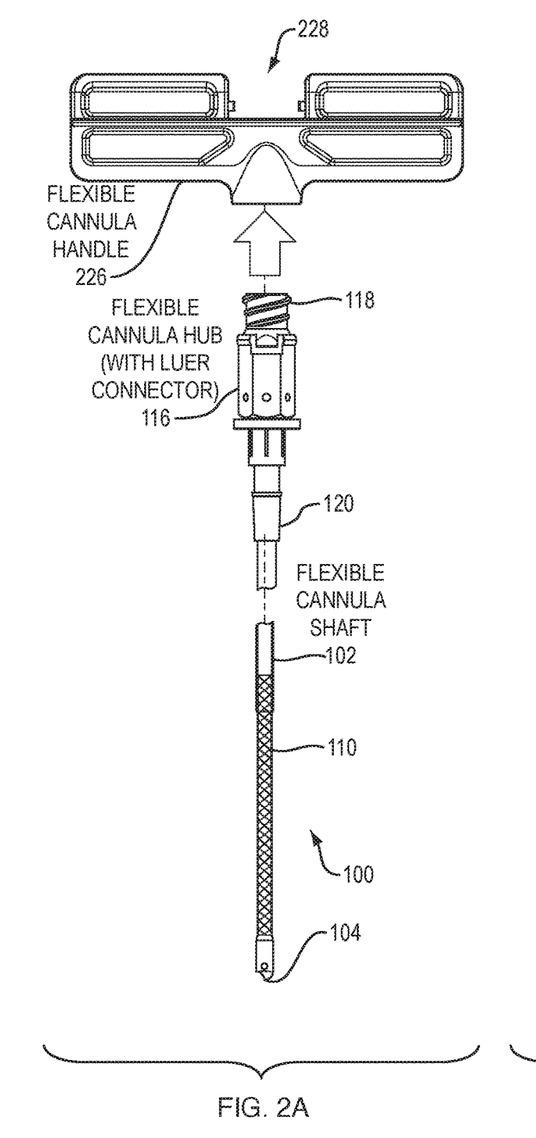
FIGS. 2A and 2B illustrate the flexible cannula of FIG. 1A including the needle hub with a handle fitted over the hub and snap fit in place.

The handle of the device can include a needle hub (see, e.g., FIG. 1A), or a hub with a winged handle assembled onto the hub (see, e.g., FIG. 2A). In an example (see, e.g., FIG. 1A), the inner cannula that fits through the coil is a PEEK tube that is molded into the needle. A winged handle can be over-molded onto the hub or the hub itself can serve as the handle.

In embodiments, the distal end of the inner tube can stop inside the cap at the distal end of the flexible cannula (see, e.g., FIGS. 1A-1E). This inner, solid tube can be thin, e.g., a thin a thin-walled metal tube, and can be welded on either end of the coil (see, e.g., FIG. 1E) or some combination thereof. For example, the inner tube can be welded into the handle on one end and welded onto the distal end of the coil on the other end. Metal tubing is preferred, as welding metal to metal is generally easier than bonding metal to a polymer, such as PEEK.

The assembled flexible cannula can be connected to a hub that has a luer connector and handle over-molded onto the needle hub on the proximal end. On the distal end, the solid tip of the cannula can be open or closed, swaged or straight walled, and can have features such as a drill tip or cutting surface to facilitate the travel of the cannula through bone or other tissue. The flexible cannula can be used to drill a path over a guide wire when the distal tip is open (i.e. a flexible cannulated drill) or otherwise used in places where a flexible drill is desired. The drill feature can be welded onto the solid tip of the flexible cannula and can take on many configurations depending on the application. In examples illustrated herein (see, e.g., FIGS. 1A-1e), the cannula has a closed cap welded to the end of the coil with a side port, the tip of the cap having a drill shaped cutting edge on the distal end. The flexible cannula can be introduced into the body through a separate cannula, e.g., an introducer cannula. This separate cannula has a lumen size where the ID (inner diameter) is greater than the OD (outer diameter) of the flexible cannula.

A flexible cannula device includes a solid cannula shaft, a solid cannula tip including an opening, and a coil positioned between and welded to the cannula shaft and cannula tip, the cannula shaft, coil, and cannula tip forming a lumen in fluid communication with the opening.

The coil can be a double helix coil comprising an inner coil within an outer coil, which can be wound in opposite directions. A tube inside the coil(s) can prevent fluid from leaking between rings of the coil(s). A cannula handle can be attached to the cannula shaft. The handle can include a luer hub secured to cannula shaft and a winged handle portion connected to the luer hub. The luer hub can include a proximal luer connector and a distal luer connector, and the cannula shaft can extend through the distal luer connector. The device can further include removable stylet receivable in the cannula shaft, the stylet including a stylet handle to couple to the cannula handle.

A flexible cannulated drill includes a solid cannula shaft, a solid cannula tip shaped to drill through tissue, a coil positioned between and welded to the cannula shaft and cannula tip, and a handle connected to the cannula shaft.

A cannula system includes an introducer needle and the flexible cannula device. The system can include a screw mechanism at the introducer needle, the screw mechanism including a lead screw and a threaded tube engaging the lead screw, rotation of the lead screw relative to the threaded tube causing adjustment of a length that the flexible cannula device extends beyond a distal end of the introducer cannula. The screw mechanism can include a first outer tube fixed to the lead screw and movably coupled to and in sealing engagement with the threaded tube. The screw mechanism can further include a second outer tube that fits over the threaded tube and the first outer tube, the second outer tube providing a gripping surface.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

As shown in FIG. 2A, the hub includes both male and female luer connections. The male luer connection is fitted over the cannula on the underside of the hub, distal to the female luer connection, which is in the upper half of the needle hub. As illustrated in FIG. 2B, the male luer connection includes an added luer lock ring snap-fit onto the male luer connection with the cannula running through the male luer connection. A stylet can be inserted through the cannula, the handle of stylet configured to couple to the handle of the flexible cannula.

DETAILED DESCRIPTION

A description of example embodiments follows.

Physiological fluids, such as bone marrow, can be aspirated using double-cannula needle assemblies. Examples of such approaches are described in the following patent applications, the teachings of which are incorporated herein by reference in their entirety:

Apparatus and methods for aspirating and separating components of different densities from a physiological fluid containing cells are described in International Application No. PCT/US2010/036696, filed on May 28, 2010 and published on Dec. 2, 2010 as WO2010/138895 A2. Apparatus and methods for aspirating tissue are described in International Application No. PCT/US2013/067358, filed on Oct. 29, 2013 and published on May 8, 2014 as WO2014/070804

A1. An aspiration device and associated method including an introducer needle assembly, an aspiration needle assembly and a screw assembly are described in International Application No.: PCT/US2015/011614, filed on Jan. 15, 2015 and published on Jul. 23, 2015 as WO2015/109100 A1. An aspiration device and method including an introducer cannula, an aspiration cannula and a mechanism (e.g., a screw assembly) to move the cannulae are described in U.S. application Ser. No. 14/885,821, filed on Oct. 16, 2015 and published on Apr. 21, 2016 as US 2016/0106462 A1.

FIGS. 1A-1D illustrate a flexible cannula device 100 according to an example embodiment. The flexible cannula 100 can be used for aspirating tissue, such as bone marrow. The device and includes a closed end metal cap or tip 104 with a cutting surface 106 and at least one side hole 108. The metal tip 104 fits over a double helix coil 110 of the device and is secured by a weld 112 (shown as two radial weld lines in FIGS. 1C-1D). A solid tube 114 is molded, on one end, to a needle hub 116 in the handle of the device, passes through the length of the coil 110, and ends on the opposite end in the closed end tip 104 that is welded onto the coil 110. In the example embodiment illustrated in FIGS. 1A-1D, the length dimensions (in inches) are as follows: B1=9.138, B2=0.250, B3=0.150, B4=1.300, B5=1.550.

As shown in FIG. 1A, the needle hub 116 includes a female luer connection 118 on the upper half (proximal portion) of the needle hub and a male luer connection 120 on the lower half (distal portion) of the needle hub, opposite to the female luer connection. The male luer connection 120 is closest to the coil 110. The solid metal shaft 102 of the cannula 100 is molded to the needle hub 116 in the handle on one end and secured by a weld 122 to the coil 110 on the opposite end. Thus, the needle hub 116 is over-molded to region 124 (FIG. 1B) of the solid cannula shaft 102 and to the tube 114 opposite to where the solid cannula shaft 102 is welded to the coil. The thin, solid flexible tube 114 is over-molded into the hub 116, such that the tube runs from the hub through the coil 110, ending just proximal of the side hole(s) 108 in the cap 104. In the illustrated embodiment, the tube 114 is a PEEK tube or liner, which lines the inside of the lumen of the cannula shaft 102 and inside of the lumen of the coil 110.

Figure 1E:
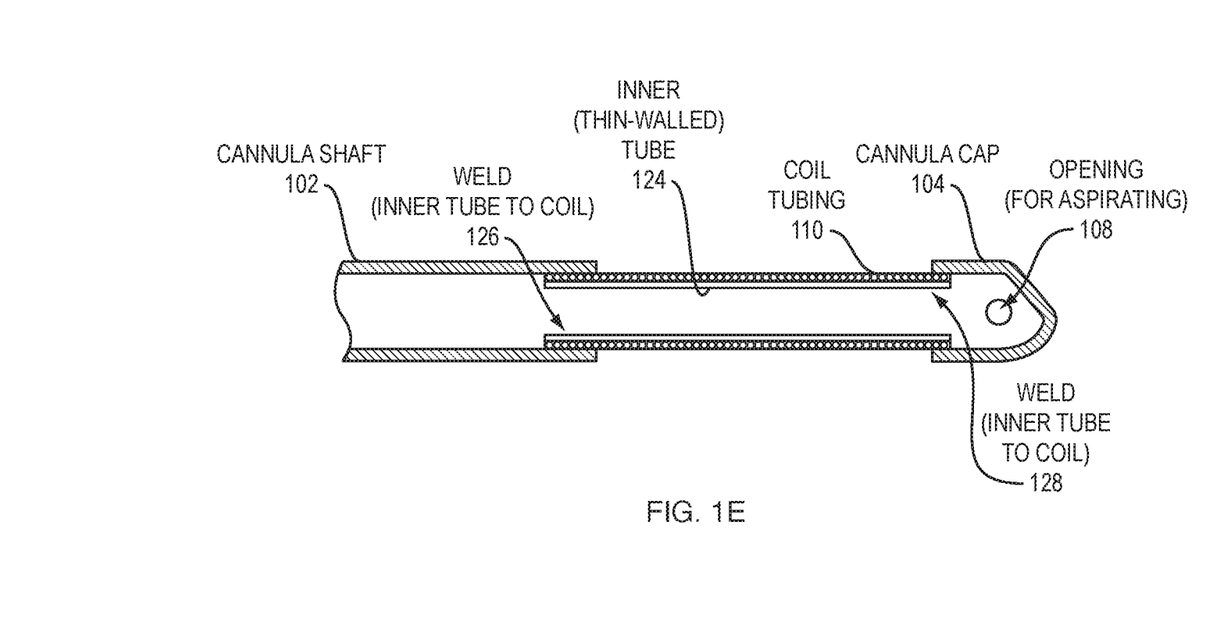
FIG. 1E schematically illustrates a thin-walled tube welded to the inside of the coil tubing, according to another example embodiment.

In an alternative arrangement illustrated in FIG. 1E, a thin-walled, metal tube 124 is placed within the coil tubing 110 and welded (126, 128) to the inside of the coil tubing, at both ends of the coil tubing, to prevent fluid from leaking between rings of the coil. As described with regarding to FIGS. 1A-1D, the coil tubing 110 itself is welded at one end to the cannula shaft 102 and at the other end to the cap 104. The cap 104 includes at least one opening 108 that is in fluid communication with the lumen of the coil 110 and the cannula shaft 102, to provide channel for aspiration.

Figure 2B:
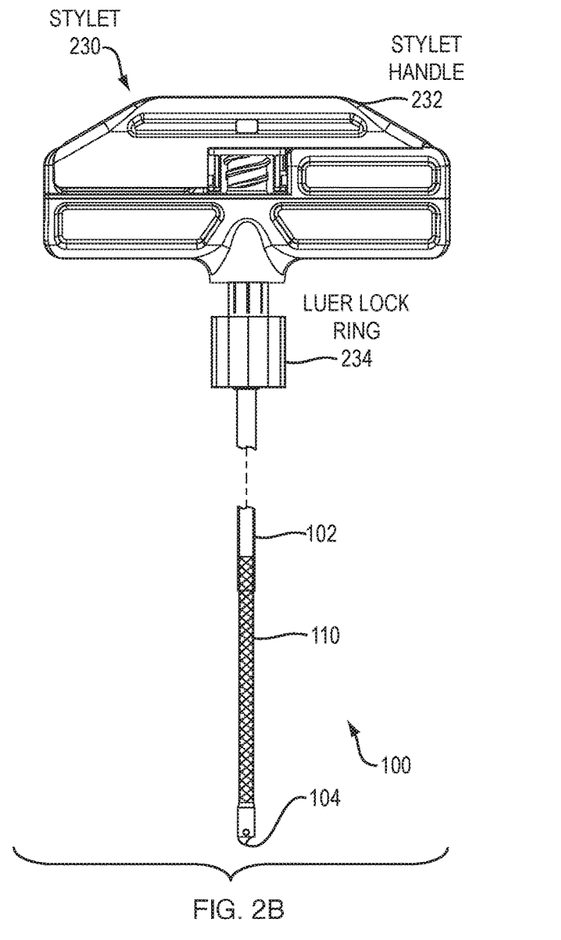

FIG. 2A shows the flexible cannula device 100 of FIG. 1A being assembled with a handle 226 that is fitted over the luer hub 116. A through-bore 228 in the handle 226 is configured to receive and engage, e.g., via snap-fit, a complementary portion of the luer hub 116, to secure the handle to the hub. A removable stylet 230 with a stylet handle 232 can be assembled onto the handle 226 that is connected to the flexible cannula 100. The hub 116 in the assembled handle has a female luer 118 on the upper side and a male luer 120 on the underside. The cannula shaft 102 passes through the center of the male luer 120. A lock ring 234 can be added to the male luer 120 on the underside of the hub 116, as illustrated in FIG. 2B. This forms a two-part handle assembly (226, 232) of the cannula 102 and stylet 230. The stylet 230 fits coaxially into the flexible cannula 100. The stylet can have varying lengths. The stylet can be long enough to dead end against the cap 104 that is welded on the distal end of the double coil 110.

FIGS. 2A-2B illustrate example handles 226 and 232 but various handle configurations are contemplated. In general, the flexible cannula 100 is meant to be advanceable into bone by either hand force, a mallet or a drill. The flexible cannula 100 can be used with or without the stylet 230. The luer hub 116 has a female luer connection 118 on the proximal end, to connect to a fluid receptacle, e.g., a syringe, and a male luer connection 120 on the distal end, to connect to another device, e.g., another cannula or needle device. The male luer 120 can have a snap fit luer threaded lock ring 234 (FIG. 2B) to facilitate a secured connection to a female luer hub, e.g. a female luer connector of an introducer cannula (see, e.g., connector 607 in FIG. 6A).

The flexible cannula device is meant to be advanced into tissue, such as bone, by a drill as one option. Various drill adapters are contemplated that allow a standard or custom drill to attach to the cannula. Such features can be accessory items or built into the handle.

Figure 3:
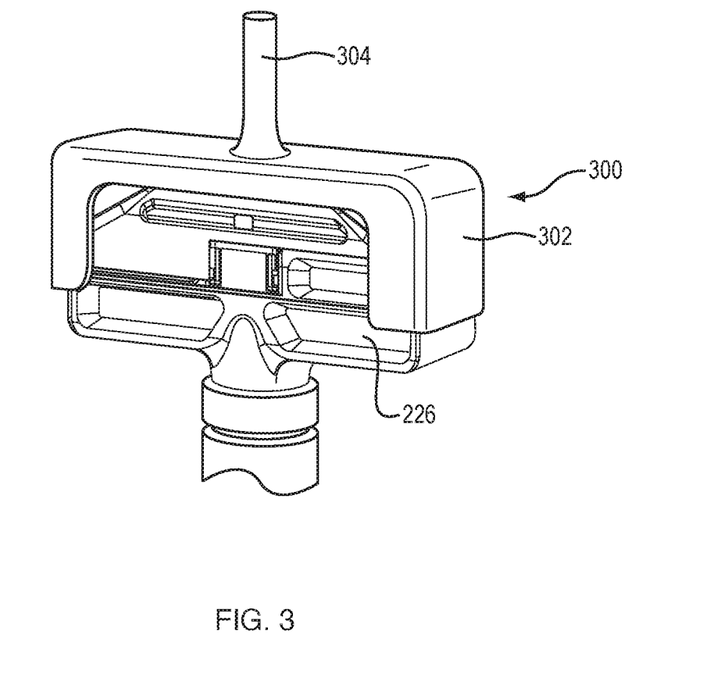
FIG. 3 shows an accessory handle used to drill the cannula and stylet into tissue.

FIG. 3 shows an accessory adaptor 300 that can be used to drill the cannula into tissue. The adaptor 300 includes a body 302 configured to attach to a handle, e.g. handle 226 of flexible cannula device 100. A stem 304 protrudes from the body 302 of the adaptor and is configured to fit a standard chuck on a drill (no shown). When the drill chuck is attached to this stem 304, the cannula is now engaged to the drill.

Figure 4A:
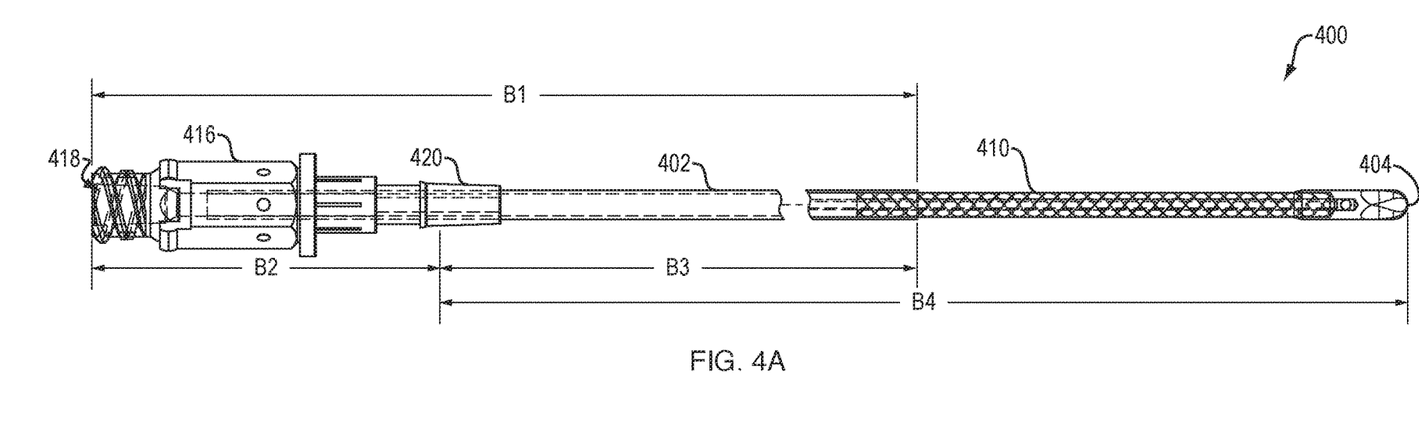
FIG. 4A illustrates a flexible cannula device including an outer metal cannula, coil tubing, a cap, and an inner tube according to another example embodiment.
Figure 4B:
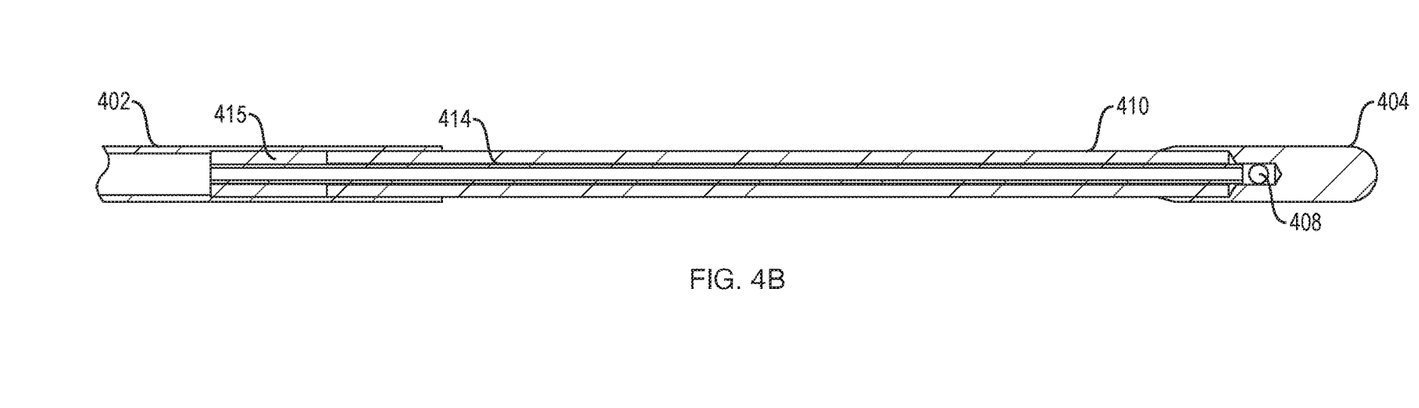
FIG. 4B is a sectional view of the distal end of the device of FIG. 4A, illustrating the inner tube extending from the cannula shaft to the cannula tip through the coil.
Figure 4C:
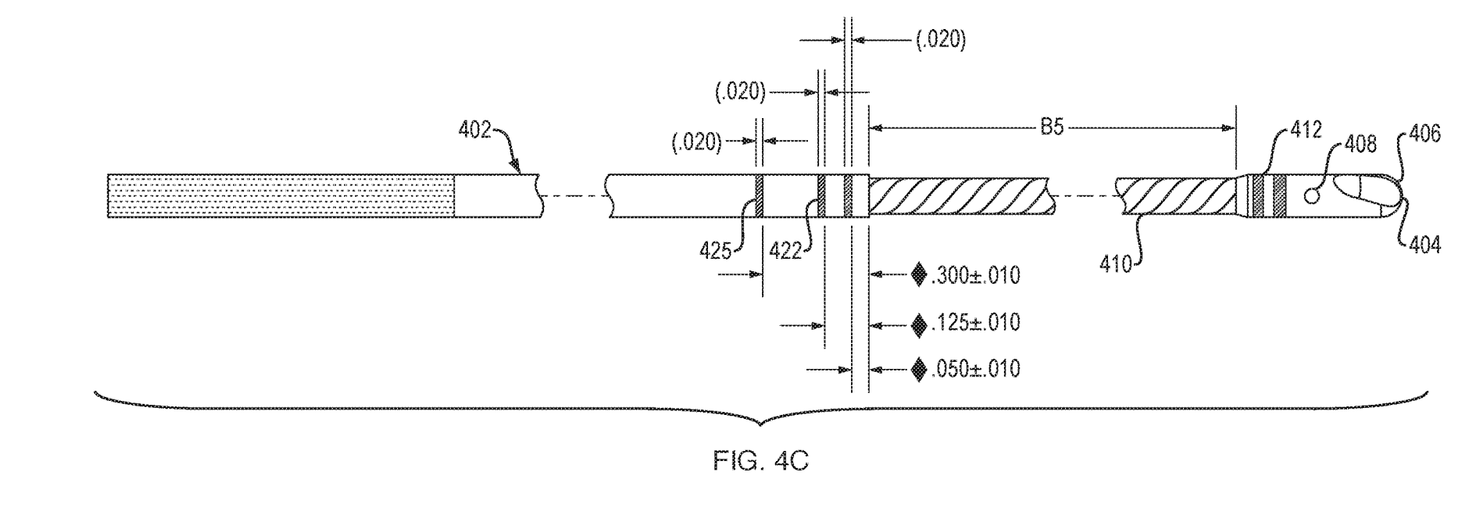
FIGS. 4C-4G are additional views illustrating elements of the flexible cannula device of FIG. 4A.
Figure 4D:
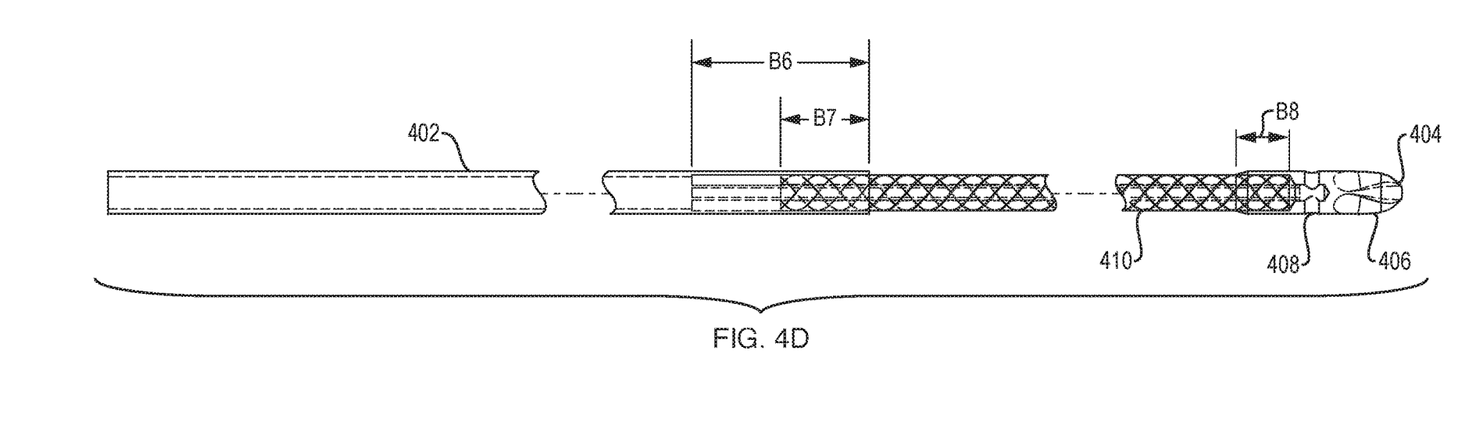
Figure 4E:
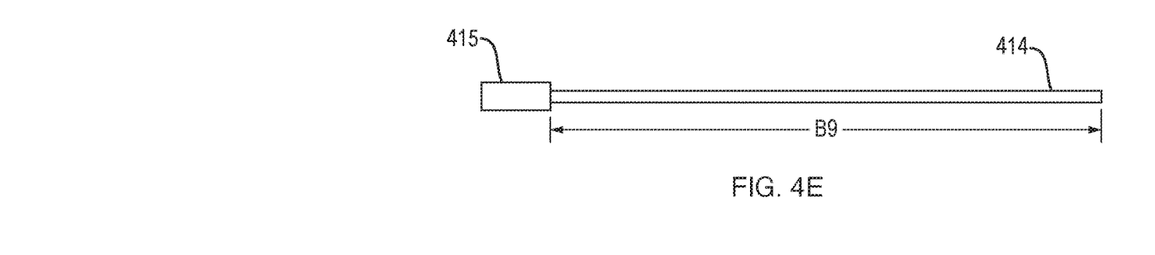
Figure 4F:
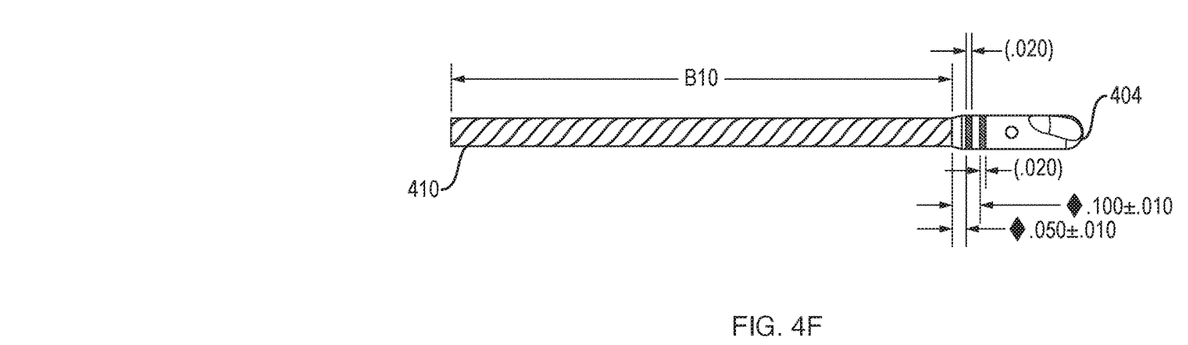
Figure 4G:
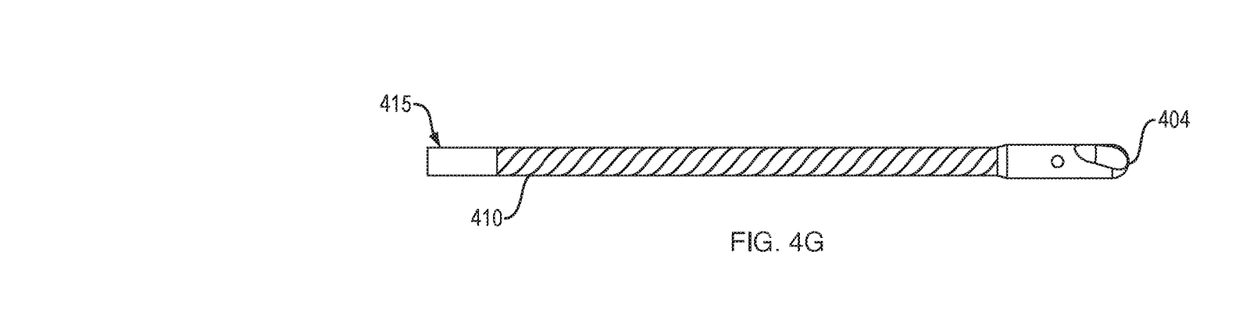

FIG. 4A illustrate a flexible cannula device 400 according to another example embodiment. FIGS. 4B-4G illustrate elements and features of the flexible cannula device 400. The device 400 is in many aspects similar to the device 100 of FIG. 1A described above. For ease of reference, corresponding elements have been numbered with corresponding reference numerals incremented by 300. For example, the device 400 includes a metal cannula shaft 402, a cap 404, coil tubing 410 positioned between the shaft and the cap, and an inner tube 414 extending through the coil tubing. The device 400 differs from the device 100 in that the inner tube 414 is metal that is secured to a bushing 415. The bushing is used to secure the tube 414 to the coil 410. The bushing 415 is welded (425) to the cannula 402. Also, the configuration of the cap 404 of device 400 differs from that of device 100, the differences including the length of the cap and the shape of the cutting surface 406 at the tip of the cap.

In the example embodiment illustrated in FIGS. 4A-1G, the length dimensions (in inches) are as follows: B1=9.191, B2=1.425, B3=7.766, B4=9.769, B5=1.550, B6=0.500, B7=0.250, B8=0.150, B9=1.980, B10=1.800.

The cap 414 includes a closed end metal tip attached (e.g., welded at 412) to the coil 410 on the coil end distal to the needle hub 416, the cap having a cutting surface 406 and side holes 408. The inner tube 414 runs substantially the length of the coil 410 and extends into the cap 404. The outer metal cannula 402 is molded into the needle hub and is attached (e.g., welded at 422) to the coil 410 on the other end. A female luer connection 418 is provided on the proximal end of the needle hub 416 and a male luer connection 420 on the distal end of the needle hub 416 opposite to the female luer connection. The needle hub 416 can serve as the handle or, as shown in FIGS. 5A-5C, a winged, removable handle can be attached to the needle hub.

Figure 5A:
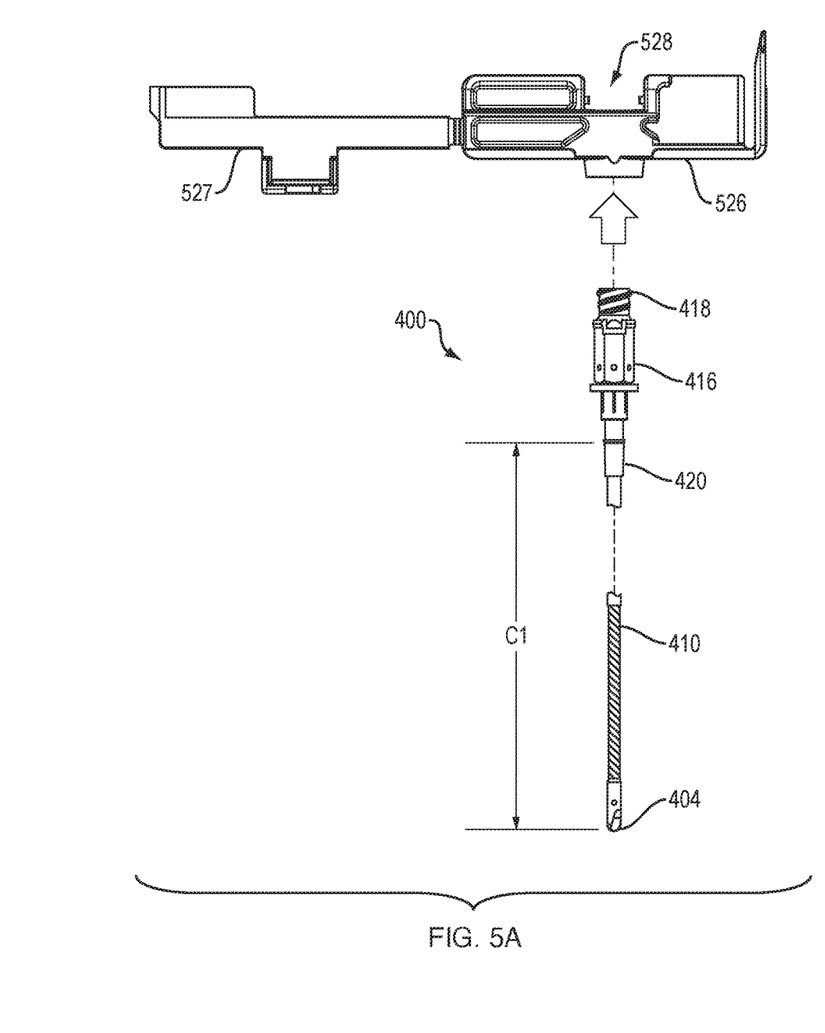
FIGS. 5A, 5B and 5C illustrate the flexible cannula of FIG. 4A including the needle hub with a removable handle fitted over the hub and a stylet receivable in the flexible cannula.
Figure 5B:
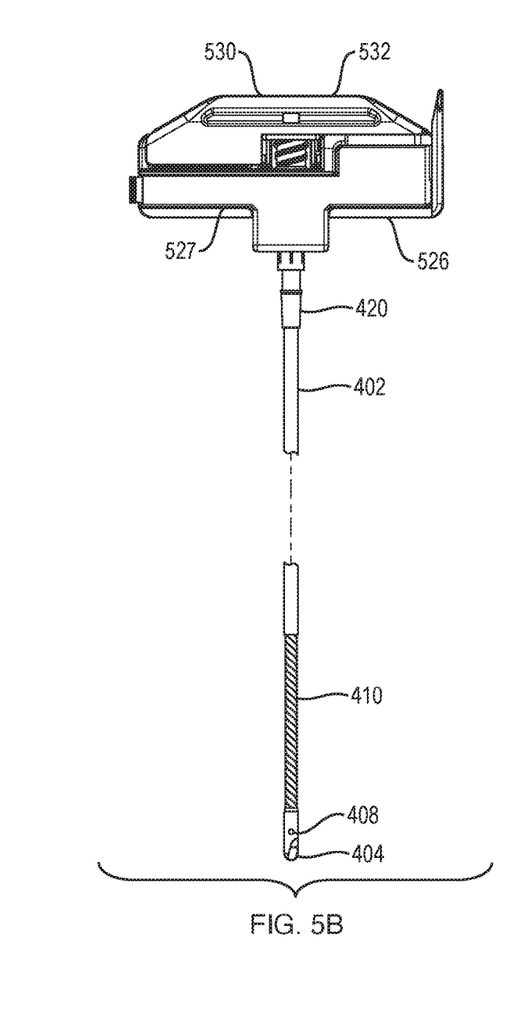
Figure 5C:
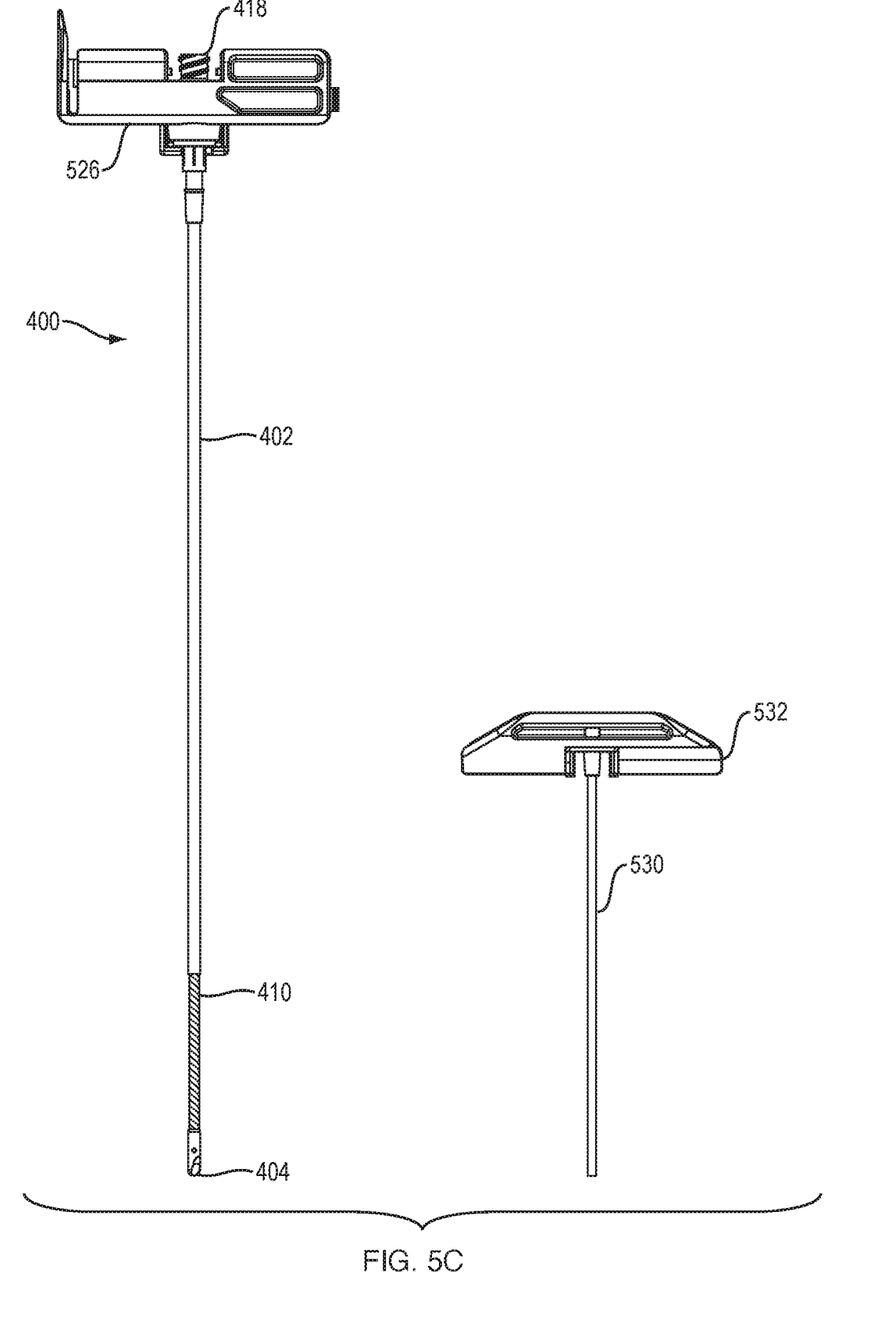

FIGS. 5A, 5B and 5C illustrate the flexible cannula 400 of FIG. 4A including the hub 416 with a removable handle 526 fitted over the hub and a stylet 530 receivable in the flexible cannula. The removable handle 526 includes a receptacle 528 that is configured to receive the hub 416. A living hinge portion 527 of the handle 526 can lock the hub 416 in place when the hinge is closed, as shown in FIG. 5B. The stylet 530 includes a stylet handle 532 that can couple to the handle 526, to secure the stylet to the cannula device. When coupled, the stylet handle 523 covers the female luer connector 418 of the hub 416. As shown in FIG. 5C, the length of the stylet 530 can be substantially shorter than the length of the flexible cannula device 400. Thus, when inserted through the cannula device 400, the stylet may only extend through the hub 416 and partially through the cannula shaft 402 (see also FIG. 7B). Unlike the flexible cannula device 100, which is provided with a luer lock ring 234 (FIG. 2B), such a lock ring is not provided in the example illustrated for cannula device 400. In the example embodiment illustrated in FIG. 5A, the length dimension (in inches) is as follows: C1=9.816.

Figures 6A, 6B, 6C:
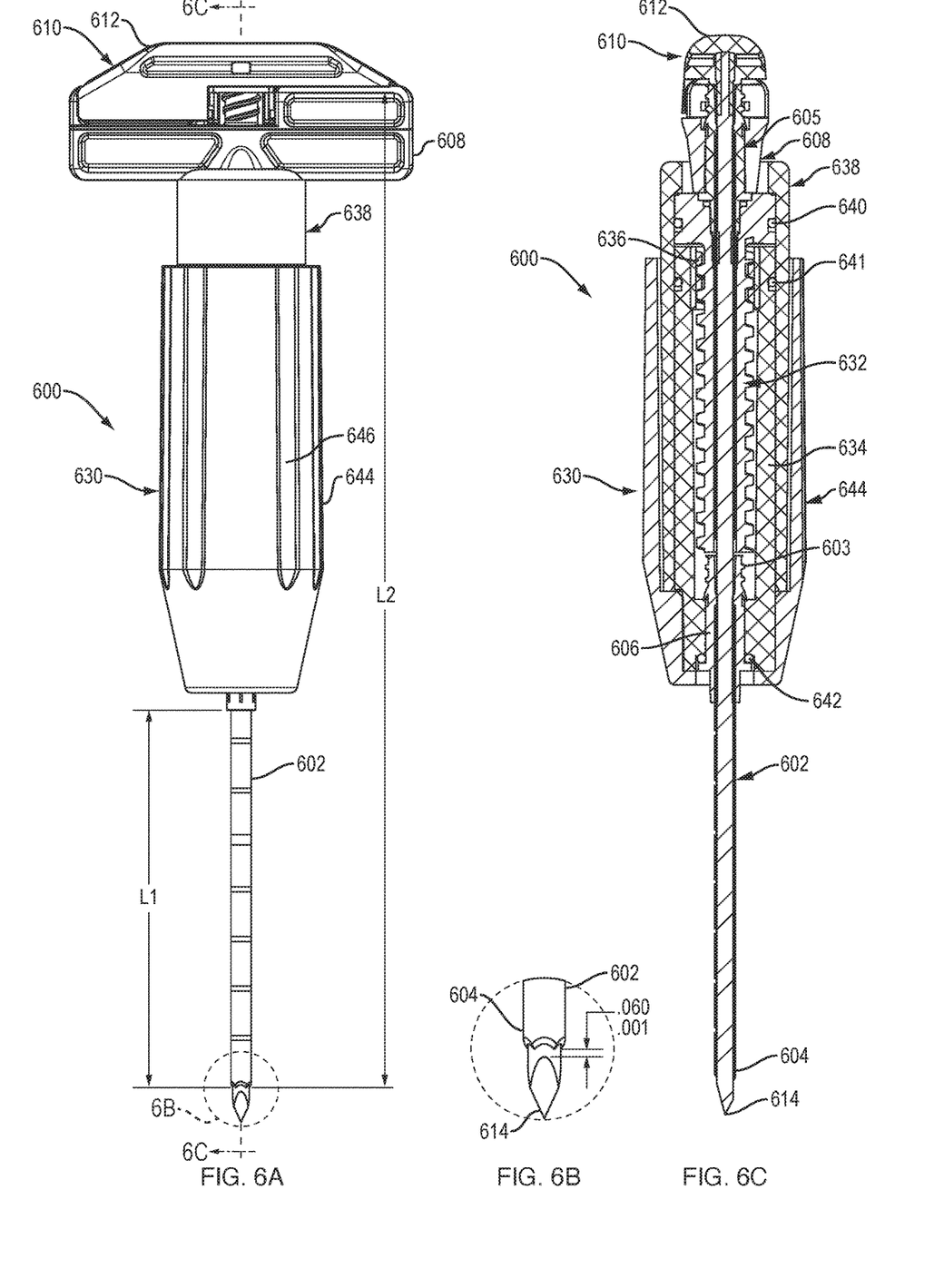
FIGS. 6A, 6B and 6C are front, detail and section views, respectively, illustrating an example access device including an introducer cannula, a removable introducer stylet, and a screw mechanism, which can be used with embodiments, including the flexible cannula devices of FIG. 1A and FIG. 5A.

FIGS. 6A-6E illustrate an access device 600, e.g., an introducer needle assembly, which is similar, in many aspects, to the device described in International Publication No. WO 2015/109100 A1, incorporated herein by reference. The introducer needle assembly 600 includes an introducer cannula 602 having a distal end 604 defining an opening and a proximal end 606 to which a hub 603 is attached. Another hub 605 is provided at the proximal end of the introducer assembly 600. The hub 605 includes a female luer connector 607 and carries a handle 608 having wings. An introducer stylet 610 is provided with a stylet handle 612 that can couple to the handle 608. The stylet 610 fits through the connector 607 and hub 605 and extends through an introducer cannula 602 at the distal end of the device 600. The stylet 610 includes a sharp tip 614 that extends beyond the distal end 604 of the introducer cannula 602 (FIG. 6B). The sharp tip 614 is configured to penetrate bone, including hard, cortical bone. A screw set 630 (e.g., a screw mechanism) is provided at the introducer assembly 600 below the introducer handle 608. The introducer cannula 602 is attached to and extends from a distal end of the screw mechanism. Attachment is via the hub 603, which connects to the threaded a tube 634. The screw mechanism 630 includes a lead screw 632 within the tube 634, which has threads 636 to engage the lead screw. The threads 636 are at a proximal end of the threaded tube 634 and can be provided by nut, which can be over-molded or otherwise incorporated into the threaded tube. The lead screw 632 can be a threaded rod with a through bore. The lead screw is attached to the handle 608 via the hub 605. A first outer tube 638 fits over the threaded tube 634 and the lead screw 632. The first outer tube 638 is connected to the fixed to the lead screw and can move relative to the threaded tube. O-rings 640 and 642 provide static seals and O-ring 641 provides a dynamic seal. A second outer tube 644 provides a gripping surface 646, which can include ridges or groves extending along a length of the second outer tube 644 (FIG. 6A).

As shown in FIG. 6A, the introducer cannula 602 extends a length L1 beyond the distal end of the screw mechanism 630. The overall length of the device 600 without the stylet 610 in place is L2, as measured from connector 607 at the proximal end of the device to the distal end 604 of the cannula 602. In the illustrated example embodiment, L1=3.0 inches and L2=7.9 inches. L1 can be up to 5.5 inches and L2 can be up to 15.0 inches. Adding length to the access device 600 would be typically mean adding corresponding length to the flexible cannula device, e.g., device 100 (FIG. 1A) or device 400 (FIG. 4A). The additional length can include increasing the length of the coil section (210, 410) of the flexible cannula device (100, 400) or the coil section could remain the same and the additional length is made from solid tubing, e.g., by increasing the length of the cannula shaft (102, 402).

Figure 6D:
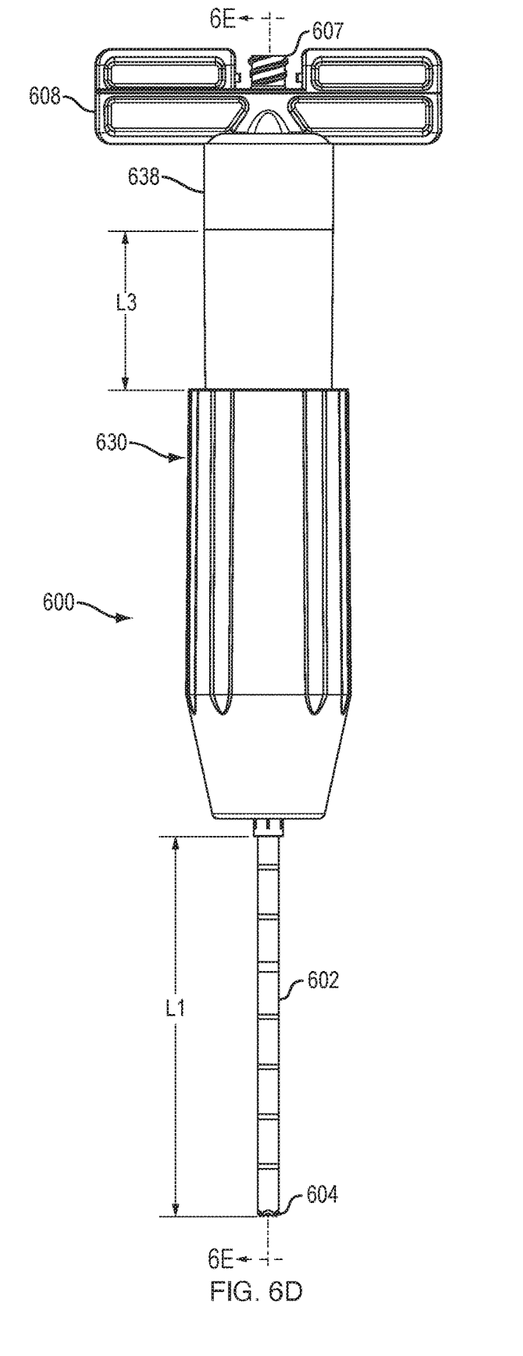
FIGS. 6D and 6E are side and section views, respectively, of the access device of FIG. 6A illustrating the screw mechanism in an expanded state and the stylet removed.
Figure 6E:
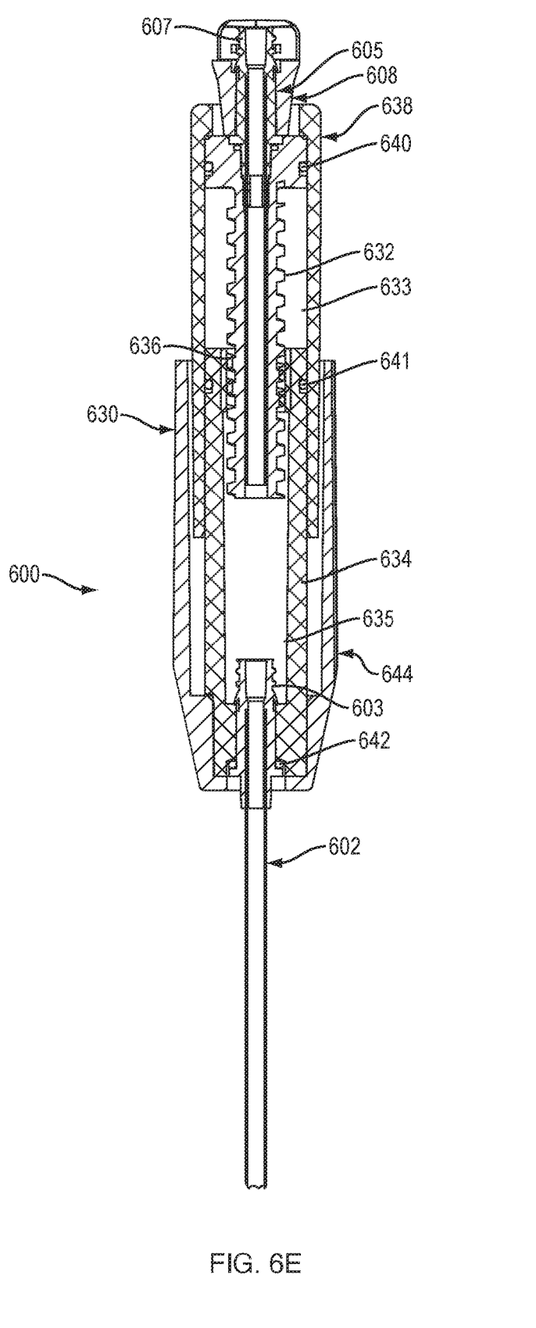

FIGS. 6D and 6E are side and section views, respectively, of the access device 600 illustrating the screw mechanism 630 in an expanded state and the stylet 610 (FIG. 6A) removed. Rotation of the handle 608 relative to the second outer tube 638 caused rotation of the lead screw 632 relative to the threaded tube 634, which in turn caused linear expansion of the screw mechanism by a distance L3. In other words, the lead screw 632 and connected hub 605 and first outer tube 634 have traveled a distance L3 relative threaded tube 634 and second outer tube 638. The expansion created spacing (e.g., separation) 633 between the proximal portion (e.g., head) of the lead screw 632 and the top end of the threaded tube 634. The expansion also created spacing 635 (e.g., separation) between the distal end of the lead screw 632 and the hub 603.

A flexible cannula device inserted through the device 600 and connected at the hub 605 also travels the distance L3 with expansion of the screw mechanism 630, as the screw mechanism moves the flexible cannula device. Any length the flexible cannula extended beyond the distal end of the device 600, e.g., the distal end 604 of cannula 602, would be shortened with the expansion. The introducer cannula 602 does not move relative to the screw mechanism 630 with rotation of the handle 608. As shown in FIG. 6D, the length L1 is unchanged relative to the length shown in FIG. 6A. Thus, the distance the introducer cannula 602 extends beyond the distal end of the screw mechanism 630 is unchanged.

Figure 7A:
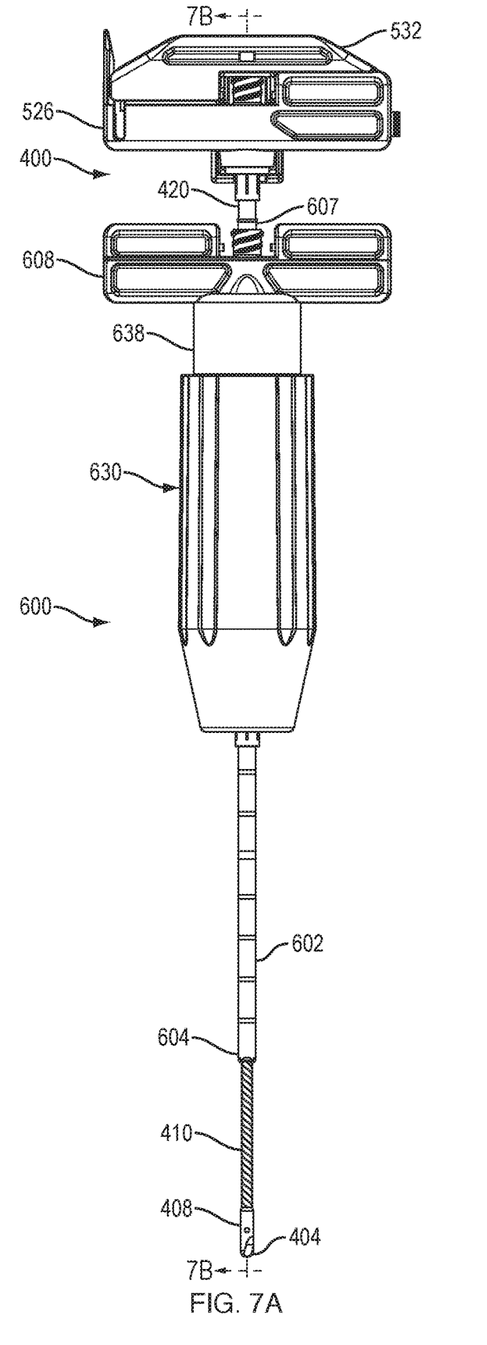
FIGS. 7A and 7B are front and section views, respectively, of the flexible cannula device of FIG. 5B inserted through the access device of FIG. 6A after removal of the introducer stylet.
Figure 7B:
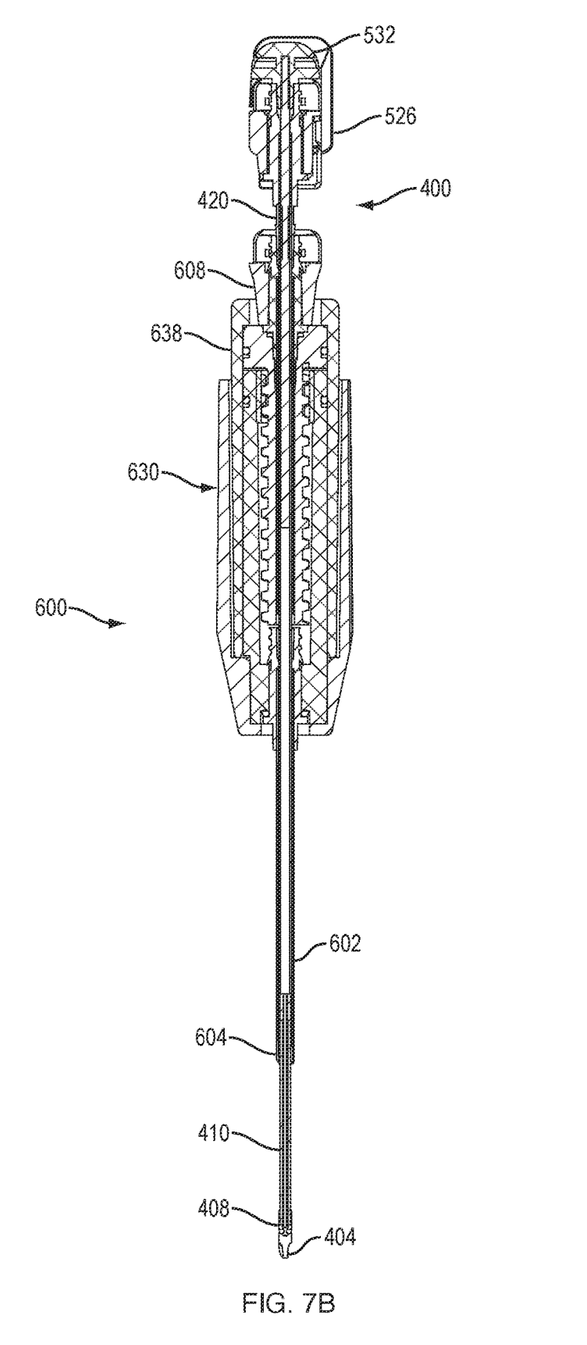

When a flexible cannula device is inserted through the introducer needle, as illustrated in FIGS. 7A-7B, rotation of the lead screw 632 relative to the threaded tube 634 causes adjustment of a length that the flexible cannula device extends beyond a distal end of the introducer cannula. The screw set 630 can be used to advance a cannula into bone and retract the cannula from the bone, as further described in WO 2015/109100 A1 (see, e.g., FIGS. 12-17C and accompanying description), incorporated herein by reference.

The flexible cannula device described herein, such as the devices 100 and 400 of FIGS. 1A-1E, 4A-4G, can be used with the introducer needle of FIGS. 6A-6E to aspirate marrow. For this purpose, one can refer to the flexible cannula as an aspiration cannula. The introducer needle 600 is inserted into the bone space with the stylet 610 in place and once the needle is positioned in the desired location (e.g., at the desired depth within the bone), the stylet is removed. The flexible cannula is then inserted through the lumen of the introducer needle 600 and advanced into the bone until the male luer connector (e.g., 120, 420) on the underside of the aspiration handle engages the female luer connector 607 in the introducer handle 608. If present, the male luer threaded lock ring 234 (FIG. 2B) on the aspiration cannula can be used to tighten the connection between the aspiration cannula and the introducer needle. If present, the stylet (e.g., 230, 530) of the aspiration cannula is then removed and a syringe is attached to the female luer connector (e.g., 118, 418) of the aspiration cannula. Aspirate can be taken through the side port(s) (e.g., 108, 408) at the distal tip of the flexible cannula using the syringe. Aspirate can be taken as the aspiration cannula is removed from the body using the force created by the screw mechanism 630 at the introducer needle 600 by turning the introducer handle 608 counterclockwise while holding the second outer tube 638.

FIGS. 7A and 7B illustrated the flexible cannula device 400 (FIG. 5B) inserted through the access device 600 after removal of the introducer stylet 610. The male luer 420 of the flexible cannula device 400 is coupled to the female luer 607 at the handle 608 of the access device 600. The distal portion of the cannula device 400 extends past the distal end 604 of the introducer cannula 602 of the device 600, such that the cannula cap 404 including side port(s) 408 are positioned distal to the distal end 604. As shown, a substantial portion of the coil 410 extends past the distal end 604 but not the cannula shaft 402. The stylet 530 is shown in place and the stylet handle 532 coupled to the cannula handle 526. To aspirate, the handles 532 and 526 are uncoupled and the stylet 530 removed, exposing the luer connector 418 (FIG. 5C) of the flexible cannula device 400.

Features and benefits of embodiments include:

The solid tube inside the coil keeps fluid from leaking through the coils. The coil can be metal and a solid thin walled metal tube can be assembled inside the coil and welded on either end of the coil to hold the tube in place inside the coil. This keeps fluid from leaking around the coils. The weld will also create an air tight seal between the outside of the inner solid tube and the coil so air cannot leak between the two assembled tubes, i.e. a solid tube inside a coil tube, as the tubes form a lumen in fluid communication with the side port(s) at the tip of the flexible cannula.

The coil can be metal and can be welded between two separate solid metal tubes on either end. As illustrated in FIGS. 1A and 4A, one of the tubes is a closed-tip cap with side port(s) for aspirating.

The coil can be metal and an inner metal tube can be welded to the coil, in a first operation, on either end. Then, in a second operation, the coil with the inner tube welded in place can be welded between two solid metal tubes on either end.

The solid inner tube that fits through the inside of the coil can be molded into a handle that has a luer connector feature.

Two solid metal cannulas (different from the solid cannula that runs through the coil) to which the coil can be welded on either end is a typical assembly for the device, i.e. proximal to distal, the flexible aspiration cannula device includes: a solid cannula shaft, a coil, and a solid cannula tip.

The proximal end of the flexible aspiration cannula device (the end opposite the cap with the side port(s) and drill tip) can be molded into a luer hub (e.g., 116, FIG. 1A), which can include or be coupled to a handle. The molded hub can include both the outer cannula and the inner tube that passes at least substantially into the coil.

The double coil prevents wobbling as the cannula is advanced or retracted.

The assembled coil drill or aspiration cannula with a handle and stylet can be introduced through another cannula (e.g., an introducer cannula, see FIGS. 6A-6E) whose ID (inner diameter) is larger than the OD (outer diameter) of the aspiration cannula.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims. For example, although access to and aspiration from bone marrow is described, devices described herein can be sue to access and/or aspirate from other tissues. Further, the devices can be used to deliver material, including, for example, biologics, to a tissue.

What is claimed is:

1. A flexible cannula device comprising:
   a) a solid cannula shaft;
   b) a solid cannula tip including an opening;
   c) a coil positioned between and welded to the solid cannula shaft and solid cannula tip, the solid cannula shaft, coil, and solid cannula tip forming a lumen in fluid communication with the opening; and
   d) a solid tube inside and secured to the coil and providing a seal, to prevent fluid from leaking between rings of the coil.

2. The device of claim 1, wherein the coil is a double helix coil comprising an inner coil within an outer coil.

3. The device of claim 2, wherein the inner and outer coils are wound in opposite directions.

4. The device of claim 3, wherein the opening is a side port.

5. The device of claim 1, wherein the solid tube extends from the solid cannula shaft and through the coil to the solid cannula tip.

6. The device of claim 1, wherein the solid tube lines the inside of the coil and at least one end of the tube is secured to at least one of the solid cannula and the coil.

7. The device of claim 1, wherein the solid tube is metal and is secured to the coil by welding.

8. The device of claim 1, further comprising a cannula handle attached to the solid cannula shaft.

9. The device of claim 8, wherein the cannula handle comprises a luer hub secured to the solid cannula shaft and a winged handle portion connected to the luer hub, the luer hub including a proximal luer connector and a distal luer connector, the solid cannula shaft extending through the distal luer connector.

10. The device of claim 8, further comprising a removable stylet receivable in the solid cannula shaft, the stylet including a stylet handle to couple to the cannula handle.

11. A flexible cannulated drill comprising:
    a) a solid cannula shaft having proximal and distal ends;
    b) a solid cannula tip shaped to drill through tissue;
    c) a coil positioned between and welded to the distal end of the solid cannula shaft and the solid cannula tip;
    d) a solid tube inside and secured to the coil and providing a seal, to prevent fluid from leaking between rings of the coil; and
    e) a handle attached to the proximal end of the solid cannula shaft.

12. The drill of claim 11, wherein the coil is a double helix coil comprising an inner coil within an outer coil.

13. The drill of claim 12, wherein the inner and outer coils are wound in opposite directions.

14. The drill of claim 11, further comprising a stylet receivable in the solid cannula shaft and coil.

15. The drill of claim 11, further comprising a removable drill adaptor coupled to the handle.

16. The drill of claim 11, wherein the solid tube is metal and is secured to the coil by welding.

17. A flexible cannula system comprising:
    a) an introducer needle; and
    b) a flexible cannula device receivable in the introducer needle, the flexible cannula device comprising:
       i) a solid cannula shaft;
       ii) a solid cannula tip including an opening;
       iii) a coil positioned between and welded to the solid cannula shaft and solid cannula tip, the solid cannula shaft, coil, and solid cannula tip forming a lumen in fluid communication with the opening; and iv) a solid tube inside and secured to the coil and providing a seal, to prevent fluid from leaking between rings of the coil.

18. The system of claim 17, wherein the coil is a double helix coil comprising an inner coil within an outer coil.

19. The system of claim 18, wherein the inner and outer coils are wound in opposite directions.

20. The system of claim 17, wherein the opening is a side port in the solid cannula tip.

21. The system of claim 17, further comprising an introducer handle at a proximal end of the introducer needle and an introducer cannula at a distal end of the introducer needle.

22. The system of claim 17, further comprising a screw mechanism at the introducer needle, the screw mechanism including a lead screw and a threaded tube engaging the lead screw, rotation of the lead screw relative to the threaded tube causing adjustment of a length that the flexible cannula device extends beyond a distal end of the screw mechanism.

23. The system of claim 22, wherein the screw mechanism further includes a first outer tube fixed to the lead screw and movably coupled to and in sealing engagement with the threaded tube.

24. The system of claim 23, wherein the screw mechanism further includes a second outer tube that fits over the threaded tube and the first outer tube, the second outer tube providing a gripping surface.

25. The system of claim 17, wherein the solid tube is metal and is secured to the coil by welding.

* * * * *